United States Patent [19]
Balkovec et al.

[11] Patent Number: 5,741,775
[45] Date of Patent: Apr. 21, 1998

[54] CYCLOHEXAPEPTIDYL AMINOALKYL ETHERS

[75] Inventors: James M. Balkovec, N. Plainfield; James F. Dropinski, Piscataway; Frances Aileen Bouffard, Scotch Plains, all of N.J.

[73] Assignee: Merck & Co., Inc., Rahway, N.J.

[21] Appl. No.: 489,976

[22] Filed: Jun. 13, 1995

Related U.S. Application Data

[63] Continuation-in-part of Ser. No. 58,656, May 4, 1993, abandoned.
[51] Int. Cl.$^6$ ............... A61K 38/12; C07K 7/64
[52] U.S. Cl. ............... 514/11; 514/9; 530/317; 530/318
[58] Field of Search ............... 514/9, 10, 11; 530/317, 318

[56] References Cited

U.S. PATENT DOCUMENTS

| | | | |
|---|---|---|---|
| 4,117,118 | 9/1978 | Harri et al. | 424/177 |
| 4,931,352 | 6/1990 | Fromtling et al. | 435/71.3 |
| 4,968,608 | 11/1990 | Giacobbe et al. | 435/71 |
| 5,166,135 | 11/1992 | Schmatz | 514/11 |
| 5,376,634 | 12/1994 | Iwamoto et al. | 514/9 |

FOREIGN PATENT DOCUMENTS

| | | |
|---|---|---|
| 851 310 | 8/1977 | Belgium . |
| 859 067 | 3/1978 | Belgium . |
| 447186 | 3/1990 | European Pat. Off. . |
| 0 447 186 | 9/1991 | European Pat. Off. . |
| 0 451 957 | 10/1991 | European Pat. Off. . |
| 459564 | 12/1991 | European Pat. Off. . |
| 462531 | 12/1991 | European Pat. Off. . |
| 486011 | 5/1992 | European Pat. Off. . |
| 0 539 088 A1 | 4/1993 | European Pat. Off. . |
| 0539088 | 4/1993 | European Pat. Off. . |
| 561639 | 9/1993 | European Pat. Off. . |

OTHER PUBLICATIONS

A. A. Adefarati, et al., *Chem. Abstract*, 114(21), p. 441, AB #203279t. (1991).

*J. Am. Chem. Soc.*, 113(9), pp. 3542–3549 (1991).

Keller–Juslen, et al., *Chem. Abstract*, 89, AB 129931w (1978).

Keller–Julsen, et al., *Chem. Abstract*, 88, AB 7377d (1979).

Schmatz, et al., *J. Protozool.*, 38(61), pp. 151–153S (Nov.–Dec. 1991).

Peter D. Walzer, et al., *Diagn. Microbio. Infect. Dis.*, 2, pp. 1–6 (1984).

Schmatz, et al., *Antimicrobial Agents and Chemotherapy*, 36(9), pp. 1964–1970 (Sep. 1992).

*Primary Examiner*—Cecilia J. Tsang
*Assistant Examiner*—Anish Gupta
*Attorney, Agent, or Firm*—Elliott Korsen; Mark R. Daniel

[57] ABSTRACT

There are disclosed compounds of the general formula

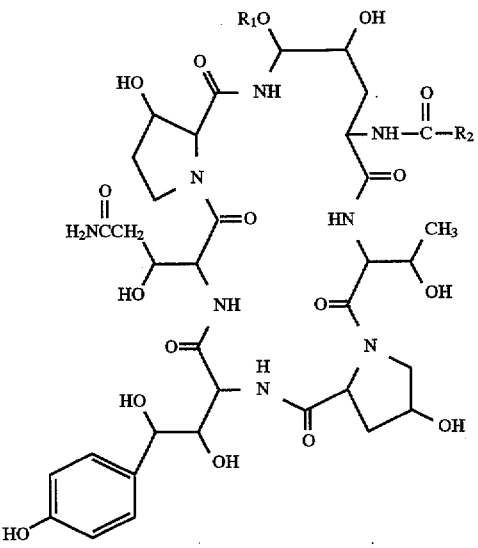

wherein all substituents are defined herein. The compounds are useful as antibiotic and antifungal agents.

8 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 1:

Xaa  Thr  Xaa  Xaa  Xaa  Xaa
    1                       5

CYCLOHEXAPEPTIDYL AMINOALKYL ETHERS

This application is a continuation-in-part of application Ser. No. 08/058,656 filed May 4, 1993, now abandoned.

BACKGROUND OF THE INVENTION

The present invention is directed to antibiotic compounds having a superior combination of properties. Echinocandin B and related fermentation metabolites are known to have antifungal properties when tested in vitro. However, some of the compounds are toxic when tested in vivo and some show lytic activity on human red blood cells thus rendering them undesirable for therapeutic use. Some derivatives have been reported as more useful compounds for human therapeutic use. Most of the derivatives are lipophilic side chain analogs at the α-amino-nitrogen of the hydroxyornithine residue or ethers at the hemiaminal position. A number of aminoalkyl ethers were prepared and are the subject of Belgian patent No. 859,067 (1978) and Belgian patent No. 851,310 (1977).

According to the present invention it has been discovered that when the aminoalkyl ether is that derived not from echinocandin B but from a cyclohexapeptide compound in which one of the nuclear amino acids is glutamine instead of threonine, the compound has superior antibiotic activity in vivo. Moreover, the compound is substantially non-toxic and also non-lytic toward human blood cells, thereby rendering the compound adaptable for human therapy which has not been possible with many compounds even though they might be active. Additionally, the compounds of the present invention have enhanced water solubility over certain cyclohexapeptides.

The compounds of the present invention are aminoalkyl ethers at the 5-position of ornithine and acyl derivatives at the $N^2$ position of the ornithine in the cyclopeptide nucleus and which may be represented by the formula (I) (SEQ ID NO 1)

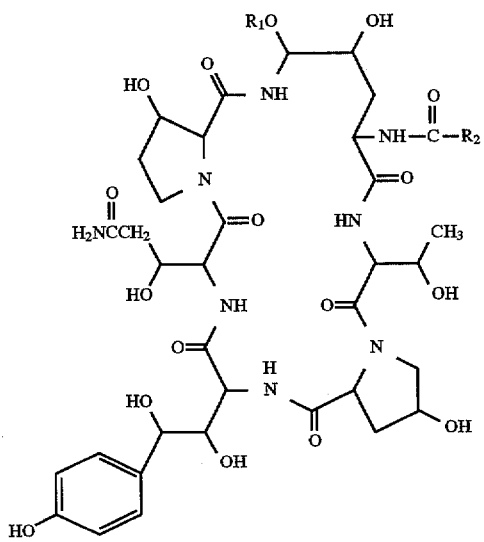

In this and succeeding formulas,
$R_1$ is
—$CH_2CH(NH_2)CH_2R^I$
—$C_nH_{2n}NR^{II}R^{III}$
—$(CH_2)_{1-3}CH(NH_2)R^{IV}$ or
—$C_nH_{2n}NHR^V$ wherein n is 2 to 6;
$R_2$ is

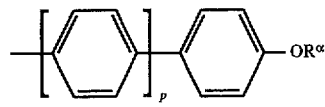

wherein
$R^a$ is $C_1$-$C_{10}$ alkyl; or $(CH_2)_q NR^b R^c$ wherein $R^b$ and $R^c$ are independently H, $C_1$-$C_{10}$ alkyl or
$R^b$ and $R^c$ taken together are

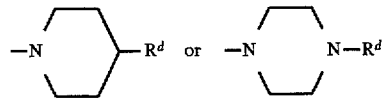

wherein $R^d$ is $C_1$-$C_{16}$ alkyl, phenyl or benzyl
$R^I$ is
—OH
—$NH_2$
—$NHC(=NH)NH_2$
—$NHC(=NH)(CH_2)_{0-3}H$
$R^{II}$ is
—H
—$C_1$-$C_4$ alkyl or
-benzyl
$R^{III}$ is
—H
—$C_1$-$C_4$ alkyl
-benzyl or
$R^{II}$ and $R^{III}$ together are —$(CH_2)_4$— or —$(CH_2)_5$—
$R^{IV}$ is
—$C_1$-$C_4$ alkyl
—$CONH_2$
$R^V$ is
—$C(=NH)NH_2$
—$C(=NH)(CH_2)_{0-3}H$
—$(CH_2)_{2-4}NH_2$
—$(CH_2)_{2-4}OH$
—$CO(CH_2)_{1-3}NH_2$
—$(CH_2)_{2-4}NH(C=NH)NH_2$
—$(CH_2)_{2-4}NH(C=NH)(CH_2)_{0-3}H$

p is an integer from 1 to 2, inclusive and
q is an integer from 2 to 4, inclusive.
The expression "alkyl" is intended to include branched and cyclic as well as straight chain radicals.

Salts of the foregoing are also within the scope of the present invention. Salts include acid addition salts and quaternary ammonium salts. These salts are formed at the amino function of the amino alkyl group. When the expression "Compound I" is employed, it is intended to embrace the salts.

Pharmaceutically acceptable salts as acid addition salts are those from acids such as hydrochloric, hydrobromic, phosphoric, sulfuric, maleic, citric, acetic, tartaric, succinic, oxalic, malic, glutamic, salicylic, lactic, gluconic, hydrocarbonic and the like, and include other acids related to the pharmaceutically acceptable salts listed in Journal of Pharmaceutical Science, 66, 2 (1977).

The compounds in the scope of the present invention which have a highly desirable combination of properties of high effectiveness and/or low toxicity and other adverse side reactions are all aminoalkyl ethers at the 5-hydroxy position of the 4,5-dihydroxyornithine component of the cyclopeptide. The amino group may be substituted or the alkyl portion may have other substituents but it is critical that the basic amino property of the group be retained.

The acyl substituent on the ornithine nitrogen differs from natural products and known compounds in being an aromatic chain of at least two phenyl groups and further extended by substituents in the para position.

Certain compounds may be named as echinocandins or pneumocandins. The compounds in which one of the amino acids of the cyclic peptide is glutamine instead of a second threonine and the side chain on the ornithine nitrogen is 10,12-dimethylmyristoyl have been named as pneumocandins by Schwartz et al, J. Antibiot. 45, No. 12, 1853–1866 (1992), and reference is also found in J. M. Balkovec et al, Tetrahedron Let., 1992, 33, 4529–32. Thus, the natural product in which the nucleus is 4,5-dihydroxyornithine, threonine, 4-hydroxy-proline, 3,4-dihydroxy-homotyrosine, 3-hydroxyglutamine and 3-hydroxyproline and the side chain is 10,12-dimethylmyristoyl is named pneumocandin $B_o$. Compounds of the present invention which differ in the substituent at the 5-hydroxy of ornithine and in the side chain acyl may be named as derivatives of pneumocandin $B_o$.

The compounds of the present invention are white solids, soluble in a variety of organic solvents such as methanol, ethanol, dimethylformamide (DMF), dimethyl sulfoxide (DMSO) and the like and also in water.

The antibiotic properties may be utilized against fungi causing pathogenic mycotic infections such as *Candida albicans, Candida tropicalis*, and the like, *Aspergillus fumigatus* and other Aspergillus sp. Additionally, the compound is adapted to be employed for inhibiting or alleviating *Pneumocystis carinii* infections, prevalent in immune compromised patients and which have usually been fatal.

The structural aspects which distinguish the compounds of the present invention is the combination of an aminoalkyl group on the 5-hydroxyornithine of the cyclopeptide nucleus, the carboxamide group arising from the nuclear amino acid glutamine, and the side chain acyl group. For the desirable combination of properties, the amino acids of the nucleus are not changed. The aminoalkyl group may be varied provided that the aminoalkyl always has a basic amino group. These modifications are those which do not affect the fundamental and essential amino acids of the cyclopeptide.

The compounds of the present invention may be prepared by aminoalkylation of a derivative of a natural product which is represented by the formula (A) (SEQ ID NO 1)

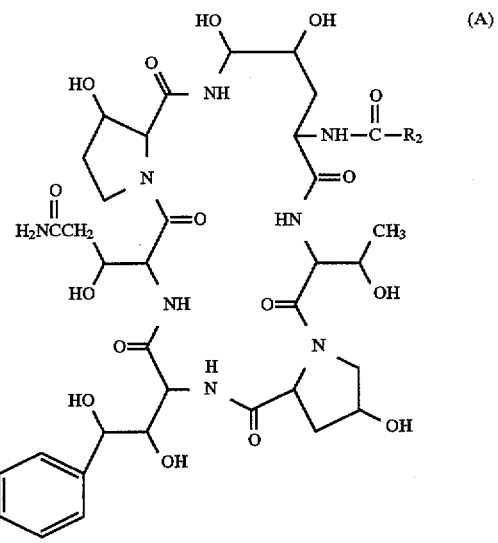

with an aminoalkanol (or alkanolamine) or substituted aminoalkanol, $R_1OH$ wherein $R_1$ is an aminoalkyl or substituted aminoalkyl group in which the amino may be substituted or unsubstituted. When it is a substituted amino group, the substituent is such that it does not neutralize the basic amino group. The aminoalkylation is carried out in the presence of a strong acid in an aprotic polar solvent and the product isolated from the reaction mixture preferably by the use of reverse phase high performance liquid chromatography (HPLC).

The nucleus of the aminoalkyl ether and the starting material are the same since the amino acids of the peptide nucleus are not changed. Thus, both product and starting material have the same Sequence ID number.

$R_1OH$ may be substituted or unsubstituted. When unsubstituted, a protecting group optionally is placed on the amino group before the reaction is carried out and the protecting group removed after the etherification is complete as hereinafter more fully described. When $R_1$ is a substituted amino group, a substituted amino alcohol may be the reactant or alternatively an unsubstituted amino alcohol may be employed and the substituent subsequently put on the amino group.

The amino alcohol is generally employed in the form of an acid addition salt and is employed in an amount of from about 20 to 200 equivalents.

The reaction is carried out in the presence of a strong acid. Examples of strong organic acids are camphorsulfonic acid, p-toluenesulfonic acid, methanesulfonic acid or a mineral acid such as hydrochloric or hydrobromic acid. Hydrochloric and camphorsulfonic acids are preferred. Approximately 1 equivalent of the acid is employed.

A solvent is employed in carrying out the reaction. Suitable solvents are aprotic solvents and include dimethyl sulfoxide (DMSO), dimethylformamide (DMF), 1-methyl-2-pyrrolidinone, hexamethylphosphoric triamide (HMPA), dioxane or combinations thereof. Dimethyl sulfoxide and dimethylformamide are preferred.

When the amino alcohol has a primary amino group, the group may be protected before it is used. Conventional protecting groups are employed. The carbobenzyloxy group (CBz) is the preferred group. In protecting the amino group with a carbobenzyloxy group, the group is placed on the amino group of $R_1OH$ by conventional means and the protected $R_1OH$, the cyclopeptide to be etherified and a strong acid, as used in the etherification using an unprotected $R_1OH$, are stirred together in a solvent such as those useful in the reaction employing an unprotected amino alcohol until substantial completion of the reaction. The progress of the reaction may be monitored by HPLC. After completion of the reaction, the reaction mixture is neutralized, diluted with water and then purified by HPLC to obtain an N-benzyloxycarbonyl aminoalkyl ether intermediate.

To obtain the desired aminoalkyl ether, the protected ether is hydrogenated under balloon pressure in the presence of palladium/carbon in acetic acid, preferably for from one to several hours as may be monitored by analytical HPLC with 30 to 40 percent aqueous acetonitrile solvent system containing 0.1% trifluoroacetic acid. The product is then recovered by first removing the catalyst and lyophilizing the filtrate to obtain the desired product as trifluoroacetate salt. The latter may be converted to a hydrochloride by passing a minimum volume aqueous solution thereof through an anion exchange column.

With substituted amino groups, if the substituent is not already on the amino alcohol, it may be placed on the amino group after the ether is formed by a method appropriate for the particular group and within the knowledge of those skilled in the art.

The ether product is isolated from the reaction mixture and is conveniently purified using HPLC techniques, including utilization of a reverse phase column. The eluants from HPLC are then concentrated and lyophilized as subsequently detailed. The elution is carried out using various concentrations of acetonitrile/water, starting at about 15 percent acetonitrile and then increasing the amount of acetonitrile. The eluting solutions generally contain 0.1 percent trifluoroacetic acid (TFA) or acetic acid and the product on isolation is found in the form of the salt.

The compounds of the present invention may be employed for the control of many fungi including the Candida species. The antifungal properties may be illustrated with the minimum fungicidal concentration (MFC) determination against certain Candida organisms in a microbroth dilution assay carried out in a Yeast Nitrogen Base (Difco) medium with 1 percent dextrose (YNBD).

For carrying out the assay, Compound I is solubilized in 10 percent dimethyl sulfoxide (DMSO) and diluted to 2560 µg/ml. The compound is then diluted to 256 µg/ml in YNBD. 0.15 mL of the suspension is dispensed to the top row of a 96-well plate (each well containing 0.15 ml of YNBD) resulting in a drug concentration of 128 µg/ml. Two-fold dilutions are then made from the top row to obtain final drug concentrations ranging from 128 to 0.06 µg/ml.

The yeast cultures, maintained on Sabouraud dextrose agar are transferred to YN broth (Difco) and incubated overnight at 35° C. with shaking (250 rpm). After incubation, each culture is diluted in sterile water to yield a final concentration of $1-5\times10^6$ colony forming units (CFU)/ml.

96-well microplates are inoculated using a MIC-2000 (Dynatech) which delivers 1.5 µl per well yielding a final inoculum per well of $1.5-7.5\times10^3$ cells. The microplates are incubated at 35° C. for 24 hours. The minimum inhibitory concentrations (MICs) are recorded as the lowest concentrations of drug showing no visible growth.

After recording the MIC, the plates are shaken to resuspend the cells. Thereafter, 1.5 µl samples from the wells in the 96-well microplate are transferred to a single well tray containing Sabouraud dextrose agar. The inoculated trays are incubated 24 hours at 35° C. and then read for minimum fungicidal concentration (MFC). MFC is defined as the lowest concentration of drug showing no growth or less than 4 colonies per spot.

The in vivo effectiveness of the compounds against fungi may be seen by the experiment carried out in the following manner:

Growth from an overnight SDA culture of *Candida albicans* MY 1055 is suspended in sterile saline, the cell concentration determined by hemacytometer count and the cell suspension then adjusted to $3.75\times10^5$ cells/ml. 0.2 milliliter of this suspension is administered I.V. in the tail vein of mice so that the final inoculum is $7.5\times10^4$ cells/mouse.

The assay then is carried out by administering aqueous solutions of Compound I ($R_1$=—$CH_2CH_2NH_2$) at various concentrations intraperitoneally (I.P.), twice daily (b.i.d.) for four consecutive days to 18 to 20 gram female DBA/2 mice, which is previously infected with *Candida albicans* (MY 1055) in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 milliters of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units (CFU) per gram of kidneys.

The compounds of the present invention may also be useful for inhibiting or alleviating *Pneumocystis carinii* infections in immune compromised patients. The efficacy of the compounds of the present invention for the therapeutic or anti-infective purposes may be demonstrated in studies on immunosuppressed rats in which Sprague-Dawley rats (weighing approximately 250 grams) are immunosuppressed with dexamethasone in the drinking water (2.0 mg/L) and maintained on a low protein diet for seven weeks to induce the development of Pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound I in 0.25 ml of vehicle (distilled water). A vehicle control is also carried out. All animals continue to receive dexamethasone in the drinking water and low protein diet during the treatment period. At the completion of the treatment, all animals are sacrificed, the lungs are removed and processed, and the extent of disease determined by microscopic examination of stained slides for the presence of cysts. The prevention of or reduction of cysts are seen in slides of lungs of treated rats when compared with the number of cysts in lungs of untreated controls or solvent controls.

The compounds of the present invention also exhibit utility against *Aspergillus fumigatus* and other species of Aspergillus.

The activity was found to be significantly greater than that found in similar compounds such as those disclosed in EP 561639.

The compounds of the present invention exhibit enhanced water solubility over similar compounds such as those disclosed in EP 561639. Some of the compounds of the invention have an aqueous solubility greater than 5 mg/ml which makes than significantly more soluble than compounds found in the abovenoted application.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound I or one of the components. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired. Compositions formulated for oral administration may be a liquid composition or a solid composition. For liquid preparations, the therapeutic may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, koalin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention and for injection take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. The compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 10 to 200 milligrams of one of the compounds.

When the compound is for antifungal use any method of administration may be employed. For treating mycotic infections, oral administration is frequently preferred.

When the compound is to be employed for control of Pneumocystis infections, it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol which may be formulated as a suspension of Compound I in a suitable propellant such as fluorocarbon or hydrocarbons.

The following examples illustrate the preparation of Compound I and compositions of Compound I useful in the therapeutic application of Compound I, but are not to be construed as limiting.

EXAMPLE 1

(Ia)

Seq. ID No. 1

Part A. Preparation of 4,5-Dihydroxyornithine-$N^2$-[4'-n-pentyloxy-[1,1',4',1''-terphenyl]-4-carbonyl]Pneumocandin $B_0$.

Pentafluorophenyl 4'-n-pentyloxy-[1,1':4',1"-terphenyl]-4-carboxylic acid (0.450 g), diisopropylethylamine (0.130 mL) and the deacylated cyclopeptide (0.70 g, 80% pure) in 12 mL of dimethylformamide were stirred at room temperature for 2.5 days. The reaction was diluted with 12 mL of distilled water and purified by preparative HPLC (Lichroprep, 40% aqueous acetonitrile to 35% aqueous acetonitrile) gave 580 mg of reacylated product (93% pure) after lyophilization. Partial $^1$H NMR (400 MHz, CD$_3$OD) δ 1.22 (d, 3H), 2.59 (dd, 1H), 2.92 (dd, 1H), 4.02 (t, 2H), 4.71 (dd, 1H), 5.04 (d, 1H), 5.12 (d, 1H), 5.39 (d, 1H), 6.76 (d, 2H), 6.99 (d, 2H), 7.14 (d, 2H), 7.60 (d, 2H), 7.71 (m, 6H), 7.93 (d, 2H). Mass spectrum (M+Li): 1189.6.

Part B. Preparation of the Aminoethyl Ether

A solution of 4,5-dihydroxyornithine-N$^2$-[4'-n-pentyloxy-[1,1':4',1"-terphenyl]-4-carbonyl]pneumocandin B$_0$. (0.480 g, prepared in Part A), ethanolamine hydrochloride (1.6 g) and camphorsulfonic acid (0.094 g) in 8 mL of anhydrous dimethylsulfoxide was stirred at 25° C. for 5 days. The mixture was diluted five-fold with water. Prepurification was accomplished on Lichroprep C-18 (80% aqueous acetonitrile to 65% aqueous acetonitrile). The product containing fractions were combined and lyophilized to obtain the crude Compound Ib. Purification by preparative HPLC (DeltaPak, 60% aqueous acetonitrile/0.1% trifluoroacetic acid, 220 nm) gave 122 mg of the desired product (>98% pure) as the trifluoroacetate salt after lyophilization. Partial $^1$H NMR (400 MHz, CD$_3$OD) δ 1.20 (d, 3H), 2.55 (dd, 1H), 2.87 (dd, 1H), 3.71 (m, 2H), 3.82 (m, 2H), 4.01 (t, 2H), 4.75 (m, 1H), 5.06 (dd, 1H), 5.12 (dd, 1H), 5.38 (m, 1H), 6.77 (d, 2H), 7.01 (d, 2H), 7.14 (d, 2H), 7.60 (d, 2H), 7.75 (m, 6H), 7.97 (d, 2H). Mass spectrum (M+Li): 1218.4.

for a period of 18 hours. At this time, diisopropylethylamine (0.345 mL) and the deacylated cyclopeptide (0.80 g, 80% pure) and an additional 3 mL of dimethylformamide were added to the above mixture and stirring was continued for 18 hours. The reaction was diluted with 13 mL of distilled water and filtered. Purification by preparative HPLC (Delta Pak, 50% aqueous acetonitrile) gave 400 mg of reacylated product (>98% pure) after lyophilization. Partial $^1$H NMR (400 MHz, CD$_3$OD) δ 1.21 (d, 3H), 1.79 (m, 2H), 2.92 (dd, 1H), 4.01 (t, 2H), 4.70 (dd, 1H), 5.03 (m, 1H), 5.11 (d, 1H), 5.38 (d, 1H), 6.76 (d, 2H), 7.01 (d, 2H), 7.15 (d, 2H), 7.59 (d, 2H), 7.64 (d, 2H), 7.98 (d, 2H). Mass spectrum (M+H): 1135.7.

Part B. Preparation of the Aminoethylether

A solution of 4,5-dihydroxyornithine-N$^2$-[4'-n-octyloxy[1,1'-biphenyl]-4-carbonyl]pneumocandin B$_0$. (0.350 g, prepared in Part A), ethanolamine hydrochloride (1.2 g) and camphorsulfonic acid (0.0716 g) in 4 mL of anhydrous dimethylsulfoxide was stirred at 25° C. for 4 days. The mixture was diluted five-fold with water. Prepurification was accomplished on Lichroprep C-18 (80% aqueous acetonitrile to 70% aqueous acetonitrile). The product containing fractions were combined and lyophilized to obtain the crude Compound Ib. Purification by preparative HPLC (DeltaPak, 60% aqueous acetonitrile/0.1% trifluoroacetic acid, 220 nm) gave 80 mg of the desired product (>98% pure) as the trifluoroacetate salt after lyophilization. Partial $^1$H NMR (400 MHz, CD$_3$OD) δ 1.19 (d, 3H), 1.79 (m, 2H), 2.85 (dd, 1H), 3.71 (m, 2H), 3.82 (m, 2H), 4.01 (t, 2H), 5.06 (dd, 1H), 5.11 (dd, 1H), 5.35 (d, 1H), 6.77 (d, 2H), 7.01 (d, 2H), 7.14 (d, 2H), 7.61 (d, 2H), 7.69 (d, 2H), 7.92 (d, 2H). Mass spectrum (M+H): 1178.6.

EXAMPLE 2

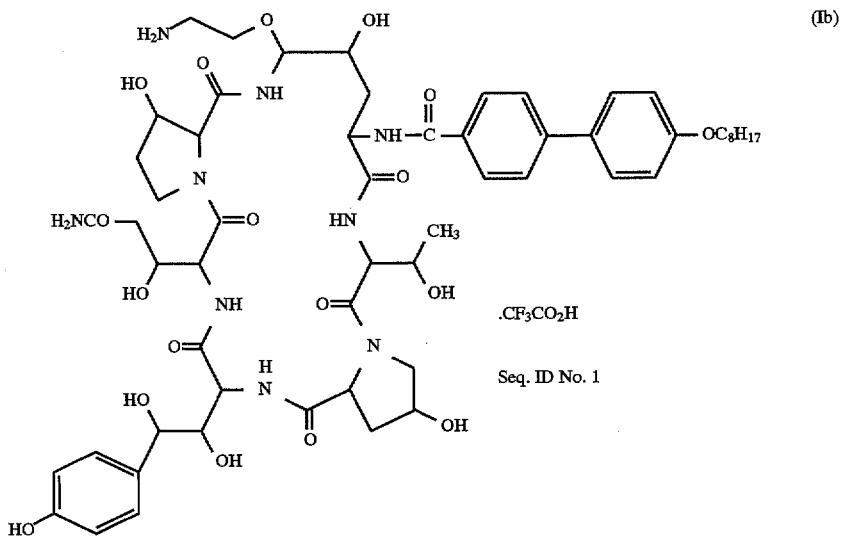

Part A. Preparation of 4,5-Dihydroxyornithine-N$^2$-4'-n-octyloxy[1,1'-biphenyl]-4-carbonyl]Pneumocandin B$_0$.

Dicyclohexylcarbodiimide (0.474 g) was added to a mixture of pentafluorophenol (0.564 g) and 4'-n-octyloxy[1,1'-biphenyl]-4-ylcarboxylic acid (0.500 g) at 0° C. in dimethylformamide. The mixture was stirred at room temperature

EXAMPLE 3

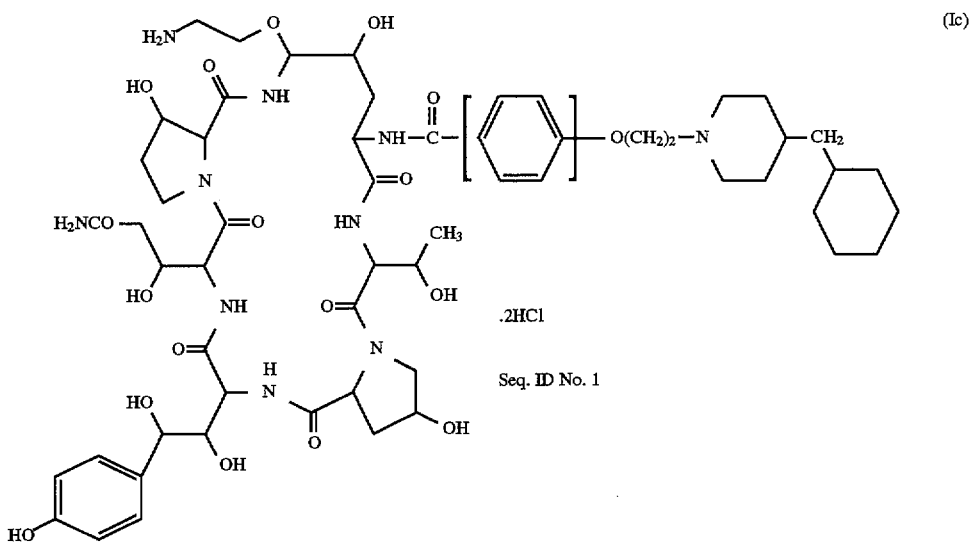

Seq. ID No. 1

In an operation carried out in a manner similar to that described in Examples 1 and 2, Compound A (where $R_2$ is

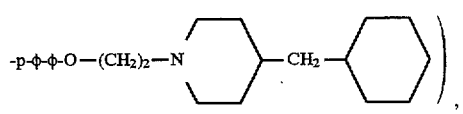

excess ethanolamine hydrochloride (36 equivalents) and 4.0M HCl in 1,4-dioxane, all in anhydrous dimethylsulfoxide are stirred together for about 2½ days or until HPLC analysis indicates conversion to a more polar product. The resulting solution is diluted with water and preparative 5% step-gradient RP18-HPLC is carried out eluting with $CH_3CN/H_2O$ (0.1% $CH_3COOH$), and monitoring at 277 nm. The product-containing fraction are combined and lyophilized to obtain the aminoethyl ether as a mixed HCl/$CH_3COOH$ salt. The mixed salt is converted to the hydrochloride salt using an ion-exchange column AG2-X8(Cl$^-$) as previously described: $C_{63}H_{90}Cl_2N_{10}O_{18}$, M.W. 1346.4.

EXAMPLE 4

In operations, carried out in a manner similar to the preceding examples, Compound Id $C_{66}H_{100}Cl_3N_{11}O_{18}$, m.w. 1442.0 is obtained.

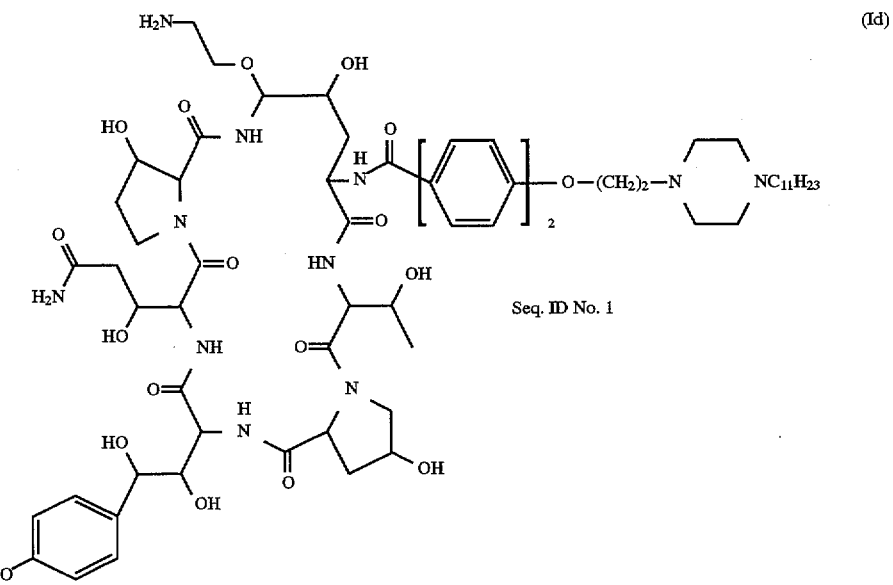

Seq. ID No. 1

EXAMPLE

In operations carried out in a manner similar to that described in the foregoing example, the following compounds are prepared:

| Example | R₁ | R₂ |
|---|---|---|
| 5 | $(CH_3)_2NCH_2CH_2-$ | 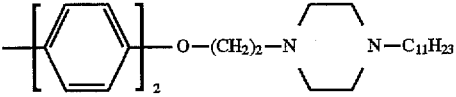 |
| 6 | $H_2NCH_2CH(NH_2)CH_2-$ | 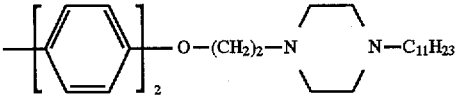 |
| 7 | $CH_3CH(NH_2)CH_2-$ | 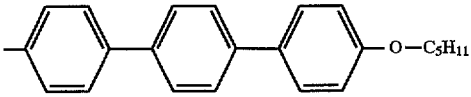 |
| 8 | $HOCH_2CH(NH_2)CH_2-$ | 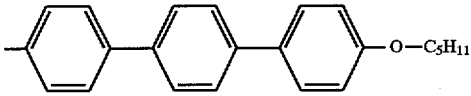 |
| 9 | $H_2N-\overset{NH}{\underset{\|\|}{C}}-NH-CH_2CH_2CH_2-$ |  |
| 10 | $H_2NCH_2CH(NH_2)CH_2-$ | 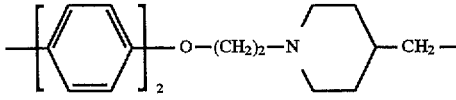 |
| 11 | $C_6H_5CH_2NHCH_2CH_2-$ | 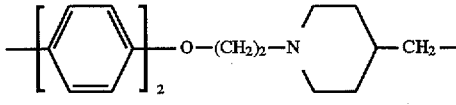 |
| 12 | $CH_3-\overset{NH}{\underset{\|\|}{C}}-NHCH_2CH_2-$ | 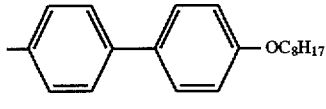 |

EXAMPLE 13

1000 hard gelatin capsules, each containing 500 mg of compound of Example 1 are prepared from the following formulation:

| Compound | Grams |
|---|---|
| Compound of Example 1 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 14

An aerosol composition may be prepared having the following formulation:

| | Per Canister |
|---|---|
| Compound of Example 1 | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE 15

1000 compressed tablets each containing 500 mg of compound of Example 2 are prepared from the following formulation:

| Compound | Grams |
|---|---|
| Compound of Example 2 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

PREPARATION OF STARTING MATERIAL

The starting material Compound A may be obtained by first cultivating *Z. arboricola* ATCC 20868 in a nutrient medium enriched in mannitol as the primary source of carbon as described in U.S. Pat. No. 5,021,341, Jun. 4, 1991 to obtain pneumocandin $B_0$. Pneumocandin $B_o$ may be converted into Compound A by subjecting pneumocandin $B_o$ in a nutrient medium to a deacylating enzyme until substantial deacylation occurs, said enzyme having first been obtained by cultivating a microorganism of the family Pseudomundaceae or Actinoplanaceae, as described in Experentia 34, 1670 (1978), U.S. Pat. No. 4,293,482 or EPA 0 451 957, Oct. 16, 1991, and thereafter recovering the deacylated cyclopeptide, and acylating the deacylated cyclopeptide by mixing together said cyclopeptide with an appropriate active ester $R_2COX$ using conventional procedures to obtain Compound I with the desired acyl group.

The active esters R'COX may be prepared by methods known to the skilled chemist as illustrated in the following examples. Although any active ester is appropriate, the compounds are illustrated with pentafluorophenyl esters.

Preparation of Alkoxyterphenyl Side Chains

The terphenylcarboxylic acid esters may be prepared through the following sequence of reactions, illustrated with a specific example as follows:

A. Preparation of pentyloxy-substituted-terphenyl-carboxylic acid:

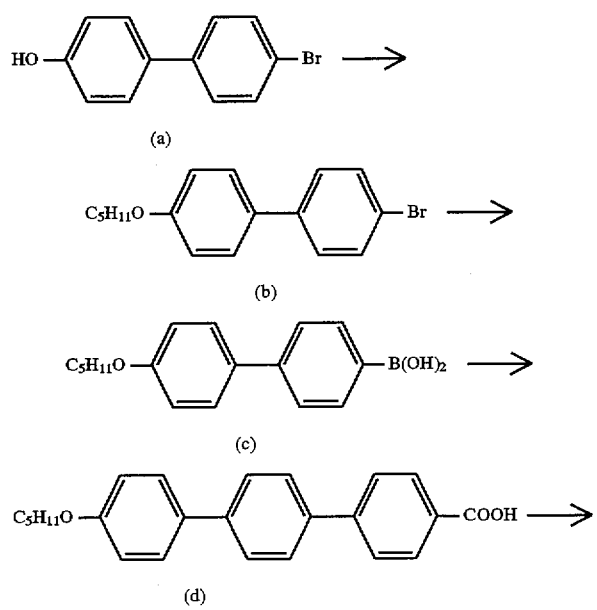

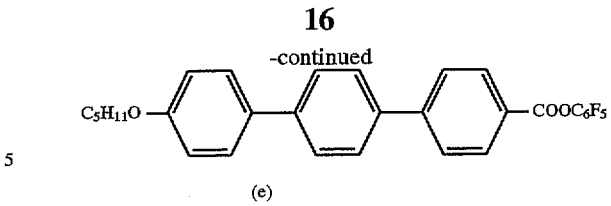

Part A: 4-(4-n-Pentyloxyphenyl) bromobenzene.

To a stirred solution of 25.5 g of 4-(4-bromophenyl) phenol (Compound (a)) in 400 mL of dimethylsulfoxide was added 40.9 mL of 2.5N NaOH, followed by 12.7 mL of n-pentyl bromide, and the resulting mixture heated at 70° C. for 18 hours to obtain in the mixture, compound (b). The mixture was partitioned between 1000 mL of ethyl acetate and 500 mL water and from the organic phase after washing with water and brine, and drying was obtained 30.9 grams of Compound (b) as a white solid.

$^1$H NMR (400 MHz, DMSO-$d_6$) δ 0.93 (t, J=7.2 Hz, 3H), 1.41 (m, 4H), 1.79 (m, 2H), 3.97 (t, J=6.6 Hz, 2H) 6.94 (d, J=8.8 Hz, 2H), 7.39 (d, J=8.6 Hz, 2H), 7.45 (d, J=8.8 Hz, 2H), 7.51 (d, J=8.6 Hz, 2H).

Part B: 4-(4-n-Pentyloxyphenyl)phenylboronic acid.

To a stirred suspension of 1.0 grams of Compound (b) in 20 mL anhydrous tetrahydrofuran at −78° C. under a nitrogen atmosphere was added 1.32 mL of 2.5M n-butyl lithium in hexanes. After 15 minutes 0.760 mL of tri-isopropyl borate was added and the stirring continued at −78° C. for 15 minutes and then at 25° C. for 40 minutes. The mixture was acidified and partitioned between ether and water to obtain the boronic acid compound (c) in the reaction mixture. The compound was recovered by washing with water and brine and drying to obtain 750 mg of 4-(4-n-pentyloxyphenyl) phenylboronic acid as white solid with the following $^1$H NMR.

$^1$H NMR (400 MHz, DMSO-$d_6$) δ 0.89 (t, J=7.2 Hz, 3H), 1.38 (m, 4H), 1.72 (m, 2H), 3.99 (t, J=6.5 Hz, 2H) 6.99 (d, J=8.8 Hz, 2H), 7.57 (d, J=8.2 Hz, 2H), 7.60 (d, J=8.8 Hz, 2H), 7.83 (d, J=8.2 Hz, 2H)

Part C: Pentafluorophenyl 4"-(n-pentyloxy)-[1,1':4',1"-terphenyl]-4-carboxylate

To a stirred mixture of 1.0 g of the boronic acid and 0.0874 mL of 4-iodobenzoic acid in 11 mL ethanol and 30 mL toluene was added 5.3 mL of a 2M aqueous solution of sodium carbonate followed by 204 mg tetrakis (triphenylphosphine)palladium and the reaction mixture heated under reflux (100° C.) for 18 hours. Thereafter, the mixture was cooled, acidified and partitioned between ethyl acetate and water. The organic phase was washed with water and brine and dried, then filtered through a bed of celite to obtain after removal of solvent and purification with flash silica gel chromatography to obtain 4"-(n-pentyloxy)-[1, 1':4',1"-terphenyl]-4-carboxylic acid.

$^1$H NMR (400 MHz, DMSO-$d_6$) δ 0.89 (t, 3H), 1.37 (m, 4H), 1.72 (m, 2H), 3.98 (t, 2H) 7.01 (d, 2H).

To a mixture of 4"-(n-pentyloxy)-[1,1':4',1"-terphenyl]-4-carboxylic acid (10.5 mmol) and dicyclohexylcarbodiimide (10.5 mmol) in ethyl acetate at 0° C. is added pentafluorophenol (11.5 mmol). The mixture is stirred at 25° C. for a period of 18 h, producing a precipitate. The mixture is filtered. The filtrate is washed with water and brine and dried with magnesium sulfate. The solvent is removed in vacuo to obtain pentafluorophenyl 4"-(n-pentyloxy)-[1,1':4',1"-terphenyl]-4-carboxylate, $C_{30}H_{23}F_5O_3$, M.W.=526.5.

Preparation of Alkoxy Biphenyl Side Chains

The biphenylcarboxylic acid esters may be obtained through the following sequence of reactions illustrated as follows:

A. Preparation of Octyloxybiphenylcarboxylic acid

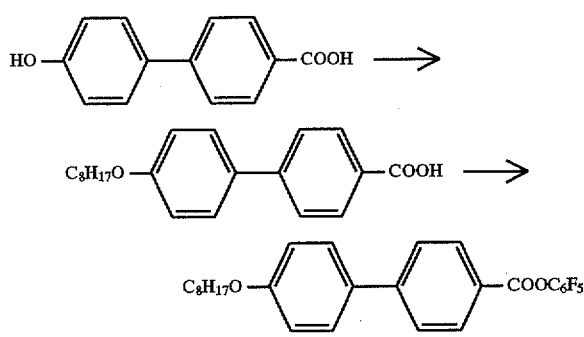

n-Octyl bromide (1.63 mL) was added to a solution of 4-(4'-hydroxyphenyl)benzoic acid (2.02 g) and 5N sodium hydroxide (3.77 mL) in dimethylsulfoxide (25 mL) and the mixture was stirred at 60°–70° C. for a period of 18 hours. The reaction mixture was cooled to room temperature and then acidified with approximately 6 mL of 2N HCl and partitioned between ethyl acetate and water. The organic phase was washed with 3×250 mL of water and 1×250 mL brine and filtered. The filter cake was saved. The organic phase was dried over magnesium sulfate and the solvent was removed under reduced pressure to obtain the 4'-n-octyloxy [1,1'-biphenyl]-4-ylcarboxylic acid (1.54 g). The filter cake from above was washed with dichloromethane and traces of the organic solvent were removed under reduced pressure to yield 1.53 g of product. The material was combined to yield a total of 3.07 g of 4'-n-octyloxy[1,1'-biphenyl]-4-ylcarboxylic acid. $^1$H NMR (400 MHz, DMSO-$d_6$) δ 0.87 (t, 3H), 1.29 (m, 8H), 1.41 (m, 2H), 1.72 (m, 2H), 4.01 (t, 2H), 7.03 (d, 2H), 7.68 (d, 2H), 7.73 (d, 2H), 7.98 (d, 2H).

B. Preparation of Pentafluorophenyl Ester

Dicyclohexylcarbodiimide (1.5 eq) was added to a mixture of pentafluorophenol (2.0 eq) and 4'-n-octyloxy[1,1'-biphenyl]-4-ylcarboxylic acid (1.5 eq) at 0° C. in dimethylformamide. The mixture was stirred at room temperature for a period of 18 hours. The crude pentafluorophenyl ester can be used directly in the reacylation of the cyclopeptide nucleus.

Preparation of Aminoethyloxy Biphenyl Side chains

Preparation of 4'-(2-[4-Cyclohexylmethylpiperidin-1-yl] ethoxy)-[1,1'-biphenyl]-4-ylcarboxylic acid. Pentafluorophenyl Ester

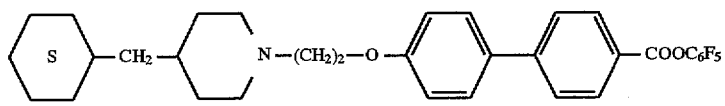

Part A: Preparation of 4-Cyclohexylmethylpiperidine

4-Benzylpiperidine is dissolved in glacial acetic acid containing $PtO_2$ (approximately 50 wt percent). A Paar hydrogenator is used and the reaction vessel is flushed with $H_2$ and pressurized to 3 atm. The mixture is shaken for sufficient time to give reduction of the aromatic ring to the fully saturated product which is determined by the uptake of 3 molar equivalents of $H_2$. The black solid is filtered and the acetic acid removed by evaporation under reduced pressure to obtain the product as an acetate salt.

Part B: Preparation of 1-(2-Hydroxyethyl)-4-cyclohexylmethylpiperidine

The product from Part A (1.0 eq) is dissolved in dichloromethane containing an equimolar amount of diisopropylethyl amine. Ethylene oxide (10 eq) is added and the mixture is stirred until starting material is consumed. The desired product is obtained by removal of the solvent in vacuo followed by purification by column chromatography.

Part C: Preparation of 4'-(2-[4-cyclohexylmethylpiperidine-1-yl]ethoxy)-[1,1'-biphenyl]-4-ylcarboxylic acid 4'-Hydroxy-[1,1'-biphenyl-4-ylcarboxylic acid methyl ester (1.0 eq) is dissolved in dichloromethane and triphenylphosphine (1.3 eq) and the hydroxyethyl compound (1.0 eq) from Part B is added. Next, diethyl azodicarboxylate (1.3 eq) is added and the mixture is stirred until starting material is consumed. The mixture is diluted with dichloro-methane and washed with water. The organic layer is dried with $MgSO_4$ and filtered. The solvent is removed in vacuo and the residue is dissolved in ethanol. An excess of 3N sodium hydroxide is added and the mixture stirred for several hours. The reaction is neutralized with 2N HCl and is extracted with ethyl acetate. The ethyl acetate layer is dried with $MgSO_4$, filtered and the solvent vaporized under reduced pressure. The desired product is obtained in substantially pure form by column chromatography.

Part D: Preparation of the Pentafluorophenyl Ester

The carboxylic acid (1.0 eq) and dicyclohexylcarbodiimide (1.0 eq) are dissolved in ethyl acetate and the solution is cooled to 0° C. Pentafluorophenol (1.05 eq) is added, the ice bath then is removed and the reaction stirred at ambient temperature for 18–24 h. An equal volume of ether is added, the mixture is filtered and the solvent removed in vacuo. The product (MW=587.64) may be obtained in a sufficiently pure form to be utilized "as is" for nucleus acylation.

Preparation of 4'-(2-[4-Undecylpiperizin-1-yl]-ethoxy)[1,1'-biphenyl]-4-ylcarboxylic acid, Pentafluorophenyl Ester

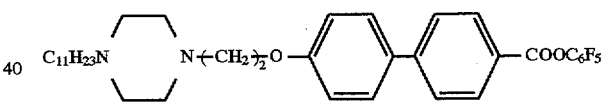

Part A: Preparation of 4-Undecylpiperazine

Excess piperazine (5 eq) and 1-bromoundecane (1.0 eq) are dissolved in dichloromethane and allowed to react overnight. The mixture is extracted with aqueous sodium bicarbonate and the organic layer dried with sodium sulfate. The mixture is filtered, the solvent removed in vacuo and the residue purified by column chromatography.

Part B: Preparation of 1-(2-Hydroxyethyl)-4-undecylpiperazine

The substituted piperazine above (1.0 eq) is dissolved in n-propanol and bromoethanol (1.0 eq) is added along with diisopropylethyl amine (1.1 eq). After several hours, the solvent is removed in vacuo and the residue dissolved in dichloromethane. The organic layer is washed with water and then aqueous sodium bicarbonate. The organic layer is dried with $MgSO_4$ and filtered. Removal of the solvent in vacuo is followed by purification by column chromatography.

Part C: Preparation of the Carboxylic Acid

The procedure is essentially the same as describe in Part C above except that the hydroxyethyl piperazine from above is substituted for the hydroxyethyl piperidine.

Part D: Preparation of the Pentafluorophenyl Ester

The procedure is identical to Part D from above except that piperazinyl-substituted-biphenyl carboxylic acid is used. The product (MW=646.75) may be obtained in a sufficiently pure form to be utilized "as is" in nucleus acylation.

---

---

What is claimed is:

1. A compound having the formula selected from the group consisting of which has a water solubility of greater than 20 mg/ml;

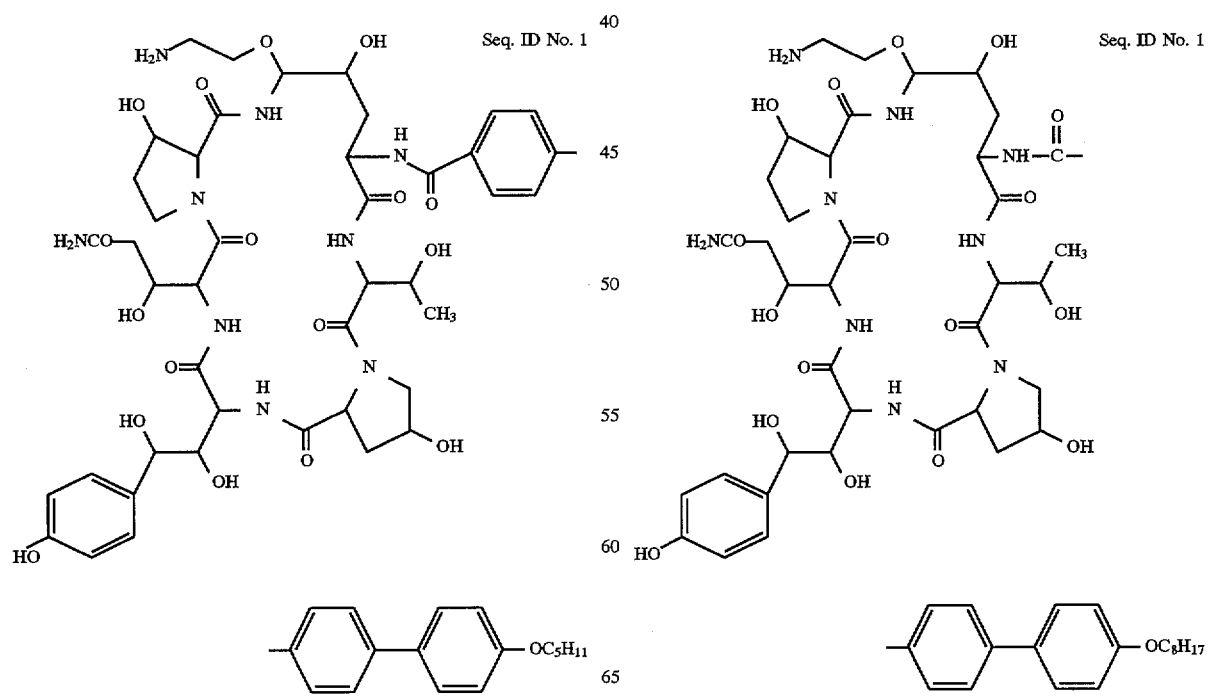

which has a water solubility of greater than 5 mg/ml;

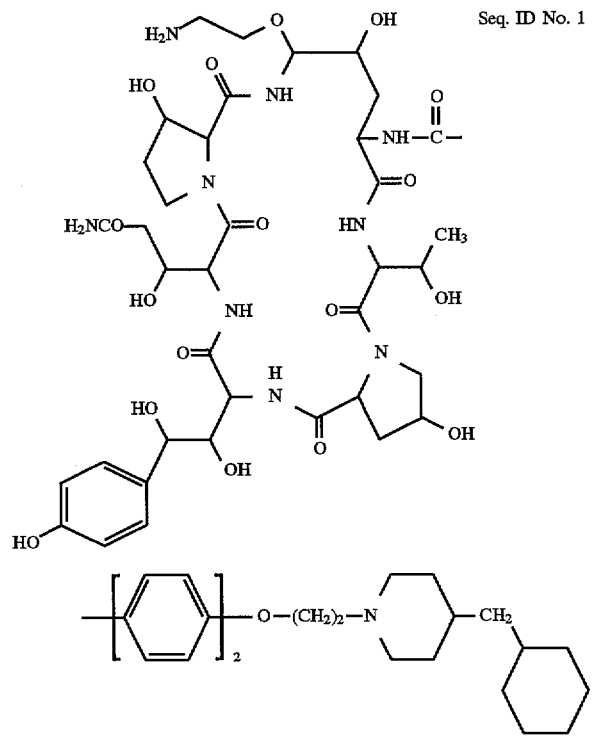

Seq. ID No. 1 and

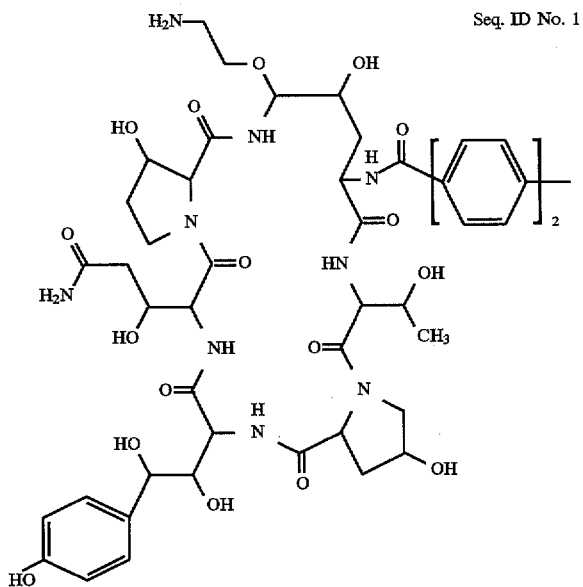

Seq. ID No. 1

-continued

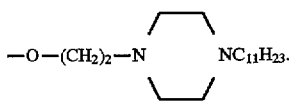

2. An antibiotic composition comprising an antimicrobial amount of a compound of claim 1 in a pharmaceutically acceptable carrier.

3. A composition according to claim 2 in unit dosage form wherein the compound of claim 1 is present in an amount of 10 mg to 200 milligrams.

4. A method for treating mycotic infections comprising administering a therapeutic amount of a compound of claim 1 to a subject in need of therapy.

5. A method for treating *Pneumocystis carinii* infections which comprises administering a therapeutic amount of the compound of claim 1.

6. A method for reducing the cysts formed in the lungs of immune compromised patients infected with *Pneumocystis carinii* which comprises administering an effective amount of the compound of claim 1.

7. A method for treating fungal infections caused by Candida sp. which comprises administering a therapeutic amount of a compound of claim 1 to a subject in need of said therapy.

8. A method for treating fungal infections caused by Aspergillus sp. which comprises administering a therapeutic amount of a compound of claim 1 to a subject in need of said therapy.

* * * * *